US008876828B2

(12) United States Patent
Lawson et al.

(10) Patent No.: US 8,876,828 B2
(45) Date of Patent: Nov. 4, 2014

(54) VERTEBRAL SURFACE PREPARATION INSTRUMENT

(75) Inventors: Jonathan Lawson, Cambridge (GB); Scott Johnson, Newmarket (GB); Robert A. Snell, Cambridge (GB)

(73) Assignee: Ranier Limited, Cambridge (GB)

( * ) Notice: Subject to any disclaimer, the term of this patent is extended or adjusted under 35 U.S.C. 154(b) by 903 days.

(21) Appl. No.: 12/428,801

(22) Filed: Apr. 23, 2009

(65) Prior Publication Data
US 2010/0274299 A1    Oct. 28, 2010

(51) Int. Cl.
*A61F 2/46* (2006.01)
*A61B 17/16* (2006.01)
*A61B 17/32* (2006.01)
*A61B 19/00* (2006.01)

(52) U.S. Cl.
CPC . *A61B 17/1659* (2013.01); *A61B 2017/320028* (2013.01); *A61B 2019/304* (2013.01); *A61B 17/1671* (2013.01)
USPC .............................. 606/86 R; 606/84; 606/85

(58) Field of Classification Search
USPC ....... 451/356, 357, 359; 606/86 R, 79, 83–85
See application file for complete search history.

(56) References Cited

U.S. PATENT DOCUMENTS

| 5,342,365 | A | 8/1994 | Waldman | |
|---|---|---|---|---|
| 5,759,093 | A * | 6/1998 | Rodriguez | 451/356 |
| 6,562,045 | B2 | 5/2003 | Gil et al. | |
| 6,896,680 | B2 | 5/2005 | Michelson | |
| 6,966,912 | B2 | 11/2005 | Michelson | |
| 7,160,304 | B2 | 1/2007 | Michelson | |
| 2003/0187448 | A1* | 10/2003 | Michelson | 606/79 |
| 2004/0002711 | A1* | 1/2004 | Berry | 606/79 |
| 2004/0002712 | A1* | 1/2004 | Grinberg et al. | 606/79 |
| 2004/0122459 | A1 | 6/2004 | Harp | |
| 2004/0215197 | A1* | 10/2004 | Smith et al. | 606/79 |
| 2005/0065529 | A1 | 3/2005 | Liu et al. | |
| 2005/0113842 | A1 | 5/2005 | Bertagnoli et al. | |
| 2006/0089649 | A1 | 4/2006 | Ullrich, Jr. et al. | |
| 2006/0129160 | A1* | 6/2006 | Liu et al. | 606/85 |

(Continued)

FOREIGN PATENT DOCUMENTS

WO    WO 03/063727 A2    8/2003

OTHER PUBLICATIONS

International Search Report and Written Opinion for International Application No. PCT/IB2010/001093, mailed Feb. 17, 2011.

(Continued)

*Primary Examiner* — David Bates
*Assistant Examiner* — Samuel Hanna
(74) *Attorney, Agent, or Firm* — Wolf, Greenfield & Sacks, P.C.

(57) ABSTRACT

An instrument for preparing a surface of a vertebra, such as a vertebral endplate, for receipt of a spinal disc implant. The instrument includes a working tool with implements on one or more surfaces of the working tool that act on the vertebral surface. The instrument includes a rotary-to-linear translation system to cause the working tool to move; for example, from side-to-side, top-to-bottom, or along a path that includes side-to-side and top-to-bottom aspects. The rotary-to-linear translation system may include a drive shaft having a cam pin at a distal end, and a cam follower slot at an anterior end of the working tool.

34 Claims, 5 Drawing Sheets

(56) References Cited

U.S. PATENT DOCUMENTS

| | | |
|---|---|---|
| 2006/0167461 A1 | 7/2006 | Hawkins et al. |
| 2006/0206117 A1* | 9/2006 | Harp .............................. 606/85 |
| 2007/0162041 A1 | 7/2007 | Robie et al. |
| 2007/0233131 A1 | 10/2007 | Song et al. |
| 2007/0270863 A1 | 11/2007 | Melkent |
| 2008/0065082 A1* | 3/2008 | Chang et al. ................... 606/85 |
| 2008/0294166 A1 | 11/2008 | Goldin et al. |
| 2009/0216232 A1* | 8/2009 | Buford et al. .................. 606/62 |

OTHER PUBLICATIONS

Harmony Port System, Abbott Spine http://international.abbottspine.com/index.php?id=62 (printed May 12, 2008).

* cited by examiner

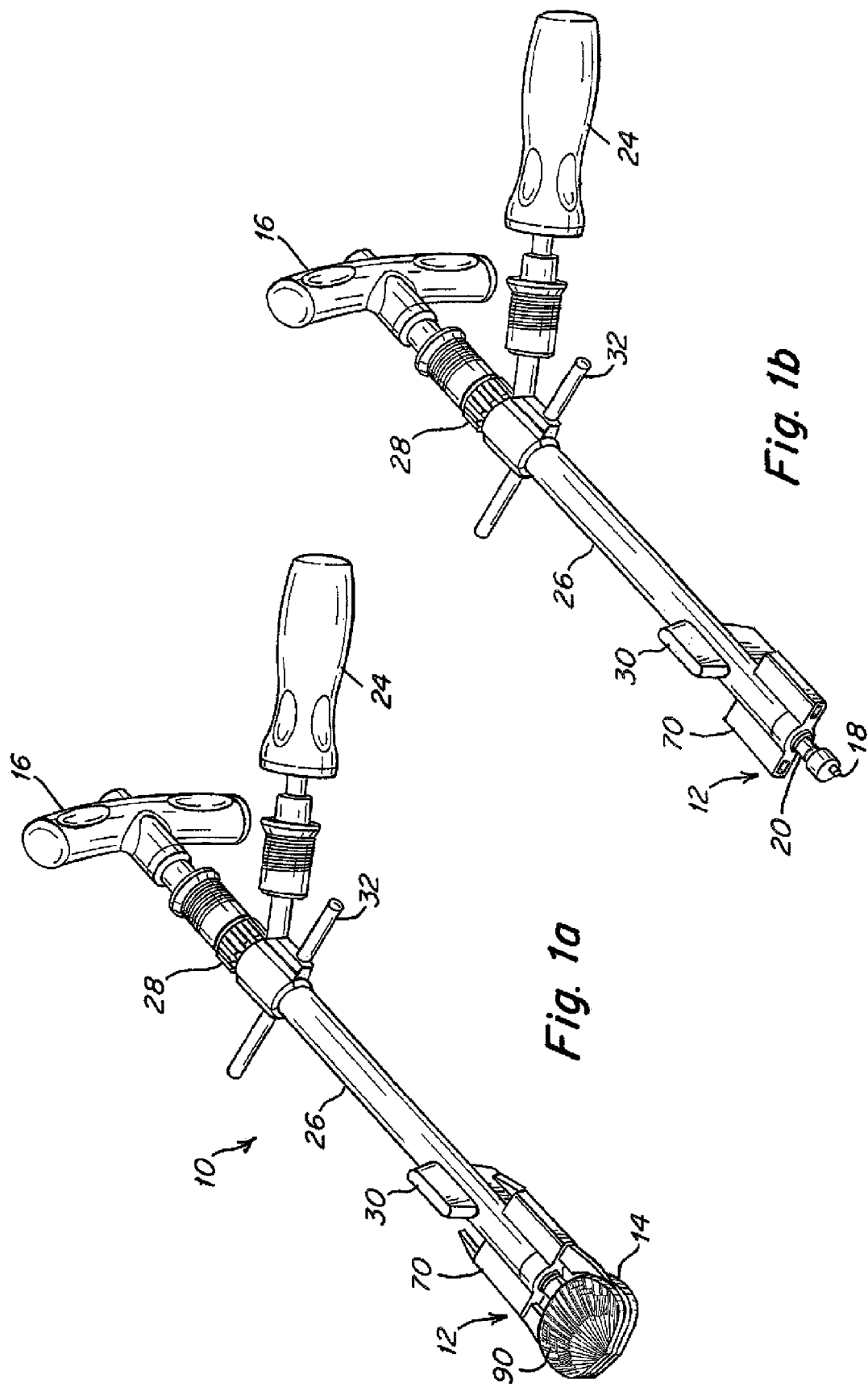

VERTEBRAL SURFACE PREPARATION INSTRUMENT

FIELD

The present invention relates to an instrument for preparing a surface of a vertebra, such as a vertebral endplate.

BACKGROUND

A spinal disc lies between surfaces of adjacent vertebrae, known as endplates. The disc stabilizes the spine and assists in distributing forces between vertebral bodies. A spinal disc may be displaced or damaged due to trauma, disease or other degenerative processes. For example, a portion of the disc may weaken or tear which can result in a protrusion into a region of the spine (e.g., the vertebratal foramen) that includes spinal nerves. The protruding portion may press against spinal nerves causing pain, numbness, tingling, diminished strength and/or a loss of motion. Another common degenerative process is the loss of fluid from the disc. Such fluid loss can limit the ability of the disc to absorb stress and may reduce its height, which can lead to further instability of the spine, as well as decreasing mobility and causing pain.

To address these conditions, a displaced or damaged spinal disc may be surgically removed from the spine and replaced with a spinal disc implant. Specialized instruments have been provided to facilitate preparation of the site which wilt receive the spinal disc implant.

SUMMARY

In one aspect, a surgical instrument is provided for preparing the surface of a vertebra. The instrument has a working end including a working tool configured for insertion between adjacent vertebra, the working tool having working implements for preparing the vertebral surface. The working tool is moveable in a direction that may be side-to-side, top-to-bottom, or along a path that includes both side-to-side and top-to-bottom aspects. The instrument includes a rotary to linear translation system for moving the working tool.

In another aspect, a vertebral surface preparation unit for use in a surgical instrument is provided. The unit includes a frame removable from and reattachable to the surgical instrument body. A working tool is configured for insertion between adjacent vertebra, and is mounted to the frame. The working tool is moveable in a direction that may be side-to-side, top-to-bottom, or along a path that may include both side-to-side and top-to-bottom aspects. The working tool includes at least a first surface with one or more working implements for preparing the vertebral surface. The working tool includes an anterior end, and an aspect of a rotary to linear translation system is accessible at the anterior end.

In another aspect, a vertebral surface preparation unit for use in a surgical instrument is provided. The unit includes a U-shaped frame including a pair of resilient, inwardly compressible legs that are adapted to releasably engage with a compatible frame mount on a surgical instrument body. A working tool, configured for insertion between adjacent vertebra, is mounted to the frame. The working tool is moveable in a direction that may be side-to-side, top-to-bottom, or along a path that may include both side-to-side and top-to-bottom aspects. The working tool including at least a first surface with one or more working implements for preparing the vertebral surface.

In a still further aspect, a surgical instrument for preparing the surface of a vertebra is provided. The instrument includes an elongated tube and a rotatable drive shaft internal to the elongated tube. A distal end of the drive shaft includes a cam pin. A working tool, configured for insertion between adjacent vertebrae, has at least one surface with working implements for preparing a vertebral surface. The working tool includes an anterior end and a cam follower slot accessible at the anterior end that is couplable with the cam pin. A frame mounts the working tool about a pivot pin. A mount is supported by the tube and is engageable with the frame, with the cam pin and the cam follower slot being couplable when the mount and the frame are engaged.

BRIEF DESCRIPTION OF THE DRAWINGS

In the drawings, each identical or nearly identical component that is illustrated in various figures may be represented by a like numeral. For purposes of clarity, not every component may be labeled in every drawing. In the drawings:

FIG. 1a is a view of a surgical instrument for preparing a vertebral surface;

FIG. 1b is a view of the surgical instrument of FIG. 1b with the working tool and frame unit removed to show the shaft and cam pin;

FIG. 2b is a view of the frame portion of the unit of FIG. 2a;

FIG. 2c is a view of the anterior end of the working tool aspect of the unit of FIG. 2a;

FIG. 2d is a view of the posterior end of the working tool aspect of the unit of FIG. 2a;

FIG. 2e is a side view of the working tool aspect of the unit of FIG. 2a;

DETAILED DESCRIPTION

Figure 1E:
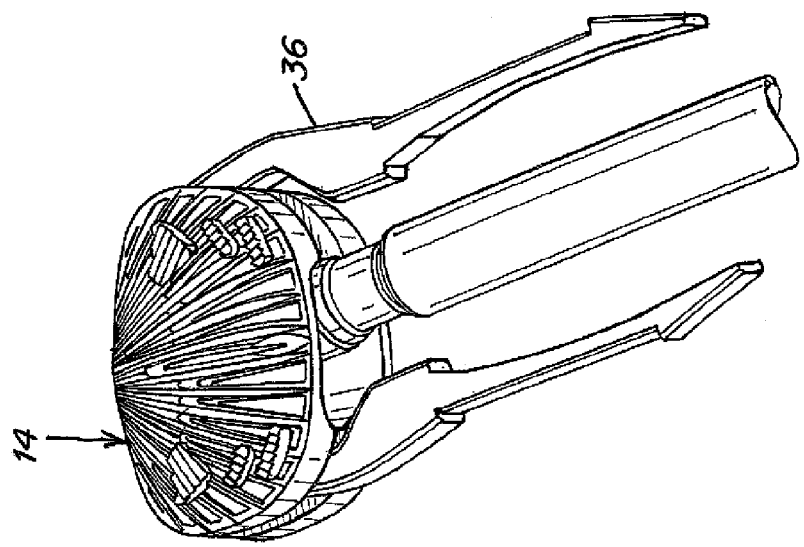
FIGS. 1c-1e are views of the surgical instrument of FIG. 1 (without the frame) showing side-to-side movement of the working tool.
Figure 1D:
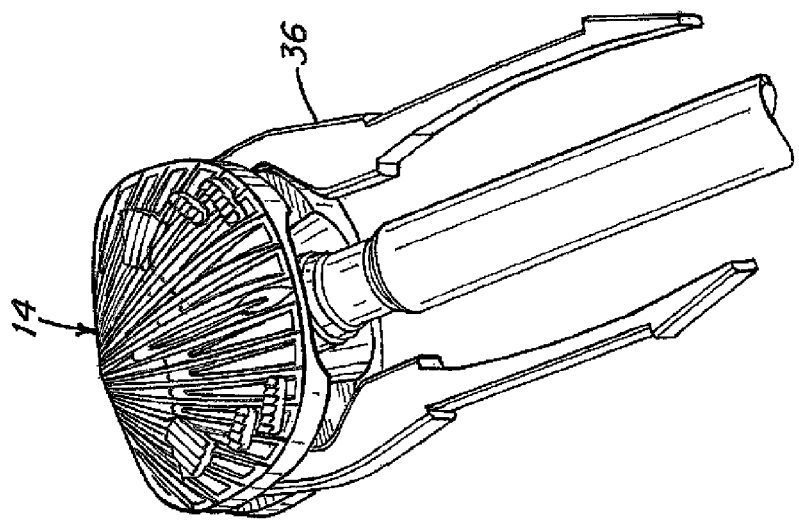
Figure 1C:
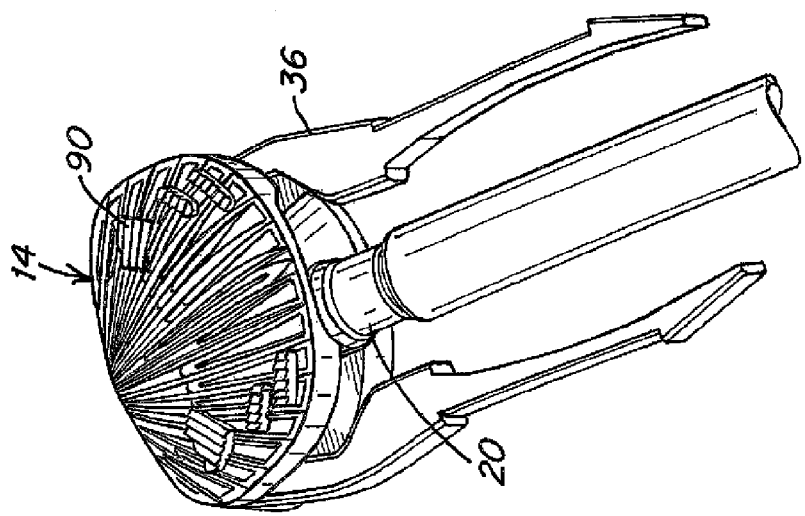

A vertebral surface, such as an endplate, may be prepared to receive a spinal disc implant and such preparation may include the formation of an endplate surface that is compatible with the adjacent contours and/or surface of the replacement disc. The spinal disc implant may include certain projections and/or other features to resist shear or rotation of the prosthetic device, to facilitate osseointegration of the implant, and/or for other purposes, and an endplate may be prepared to accommodate such projections and/or other features. An instrument suitable for such preparation of a vertebral surface is now described. Although discussed in connection with preparing an endplate or other vertebral surface, the instrument is not so limited and other applications are contemplated.

Turning to FIGS. 1a-1e and 2a-2e, an instrument 10 for preparing a surface of a vertebra, such as an endplate, includes a working end 12 having a working tool 14 that is moveable to prepare the vertebral surface. Preferably, the working tool is sweepable, that is pivotable, from either side-to-side or top-to-bottom, although other movements of the working tool are contemplated including a combination of side-to-side and top-to-bottom movements. A system for driving movement of the working tool may include a rotary-to-linear translation system, where rotation of a cam or other actuator is translated by a cam follower associated with the working tool, causing the working tool to move. In the arrangement shown, a rotary-to-linear translation system includes a cam pin 18 at a distal end of a rotatable shaft 20 and a cam follower slot 22 located in the working tool. The cam pin is received in the cam follower slot, such that rotation of the shaft turns the cam, which rotational force is translated by the cam follower into the desired movement, such as sweeping, of the working tool.

A functional handle 16 at a proximal end of the instrument may be coupled, directly or indirectly, to the shaft, so that rotation of the handle, turns the shaft and, in turn, drives the cam and cam follower system. The handle may be integrally connected, or releasably joined, to the shaft. The instrument may include an elongated outer tube 26 with the shaft extending through and being rotatable within the outer tube. A collar 28 may be threaded to the outer tube, centering and assembling the shaft within the outer tube. Unthreading the collar allows removal of the cam shaft, for example when sterilizing the instrument. A side-arm handle 24 may be provided to facilitate positioning of the instrument and may be removeable, such as from an underlying post, if desired, to avoid encumbering the field of view. One or more alignment fins 30 may be provided on the outer tube to cooperate with complementary alignment features in an associated device, such as a vertebrae distractor. Depth stop rods 32 may be provided for use with an instrument positioning system in such an associated device.

As observed earlier, in certain embodiments the working tool may be configured to sweep from side-to-side. The limit, or angle of sweep, of the working tool may characterized by reference to a sweep axis and may be the same (i.e., symmetric) along each side of the working tool. Alternatively, the working tool may be arranged so that different sweep angles (i.e., asymmetric) are provided at each side. A sweep axis may be provided at a centerline of the working tool, along a distal end. Alternatively, the sweep axis may be provided off-center and, or alternatively, closer to the proximal end of the working tool. In the latter scenario, for example, a greater arc of sweep results at the distal end of the working tool. The invention is not limited to a particular location of a sweep axis and other arrangements are contemplated including, for example, locating a sweep axis at the center of the working tool. Representative sweep angles include: +/−11.5° (total sweep angle of 23°), +/−10.5° (total sweep angle of 21°), and +/−9.5° (total sweep angle of 19°). The invention is not limited to the particular sweep angles noted, and other sweep angles are contemplated.

Figure 2A:
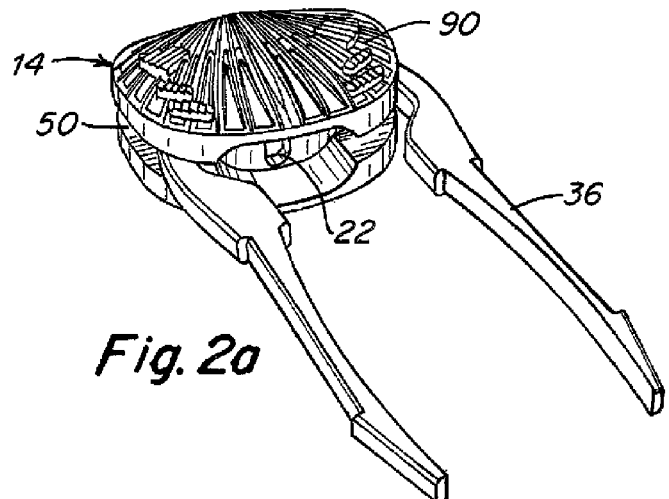
FIG. 2a is a view of a vertebral surface preparation unit.
Figure 2B:
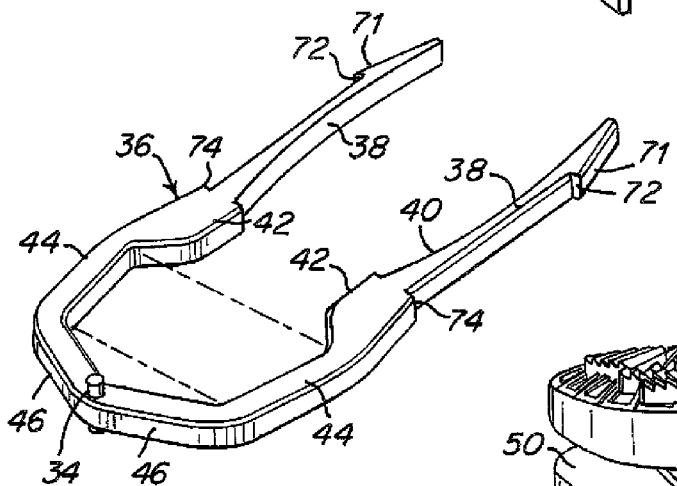
Figure 2C:
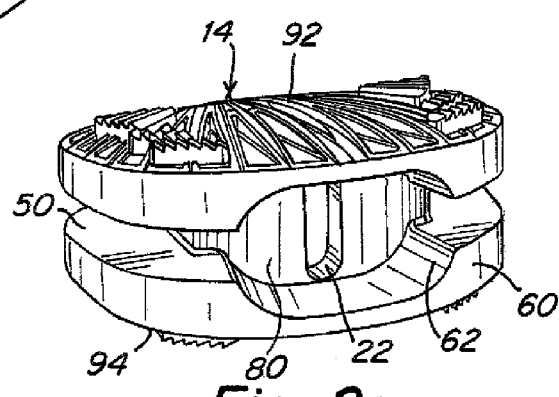
Figure 2D:
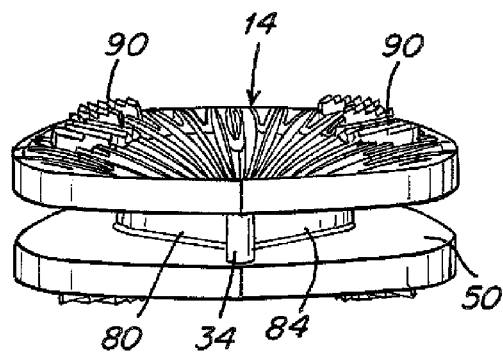
Figure 2E:
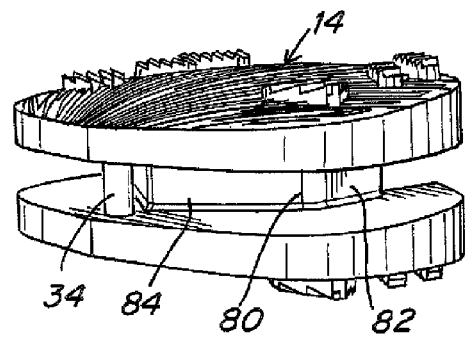

In one embodiment, a pivot pin 34 is provided at the sweep axis and the working tool moves about the pivot pin. The pivot pin may be a separate component or may be integrally formed with the working tool. A frame 36 may be provided which supports the pivot pin, and the working tool may include a hole, recess or other arrangement for cooperating with the pivot pin. The frame may be of a planar form, and have a generally U-shape. In the embodiment shown, the frame is formed of metal (although the invention is not so limited) and includes a pair of legs 38 that are each characterized by a thin proximal segment 40 that may have a slight, outwardly bowed shape, an outwardly diverging intermediate segment 42 that may include a wide shoulder, a first converging segment 44 and then a second, more acutely, converging segment 46. The first and second converging segments of each leg together define an opening having a compound shape including a distal triangular shape and a proximal quadrilateral shape (see dashed lines in FIG. 2b). As shown in FIG. 2b, a hole may be provided along a centerline and at the distal-most end of the frame, at the junction of the acutely converging segments, to receive the pivot pin. Alternatively, the pivot pin may be located elsewhere on the frame. For example, a portion of the frame may project inwardly, or a separate cross-bar may extend between sides of the frame, to provide a more proximal location for the pivot pin. In certain embodiments, the pivot pin may be integral with the frame. The relative thickness and shape of the various segments of the frame, and the relative angles therebetween, are not necessarily a limitation of the invention, and other dimensions, angles and shapes of the various segments, and the overall frame itself are contemplated. A commonly sized frame may be used with different working tools of varying size and/or of varying sweep angle. Other arrangements for pivotally mounting the working tool with the frame are contemplated.

Recesses 50 may be arranged in the sides of the working tool to receive a portion of the frame legs, such as the first and second converging segments, and may be of a sufficient depth so that the side of the working tool projects outwardly beyond the juxtaposed portion of a leg when the working tool is at its farthest extent of sweep. A standoff 80, exposed by the recesses, separates the top and bottom portions of the working tool and may have a compound shape including a proximal, generally quadrilateral shape 82, and a distal generally triangular configuration 84. The standoff is smaller than the opening between the first converging segments, ensuring freedom of movement of the working tool. Interior faces of the working tool that have been exposed by the recesses may include a bottomed out hole for receiving the pivot pin. Neither the frame, the recesses, the standoff, nor the pivot pin connection are limited to the particular configurations just described.

The proximal end 60 of the working tool, also referred to as an anterior end in connection with an instrument for preparing a vertebral surface for implantation of a spinal disc, includes an elongated slot 62 that extends in a side-to-side direction. The elongated slot provides access to a cam follower slot 22 that may extend, as shown, in a first surface (e.g., top) to second surface (e.g., bottom) direction, so that the cam follower slot extends in a direction substantially perpendicular to the elongated slot. The cam follower slot is provided in the floor of the elongated slot and, as such, the elongated slot may be characterized as a counter-bore with respect to the cam follower slot. The invention is not limited to the particular shapes of the elongated slot and the cam follower slot, and other shapes for one or both may be employed. Although shown as extending linearly, either slot may be curved or have other non-linear orientation. The elongated slot and cam follower slot need not be substantially normal to each other, and other relative axial directions also are contemplated. The elongated slot is sized to receive an end of the elongated shaft, while the cam follower slot is sized to receive the cam pin at the end of the shaft. When the cam pin is mated with the cam follower, rotation of the cam by the shaft will cause the working tool to sweep reciprocally from side-to-side. Alternatively, the cam follower slot may be arranged to move the working tool in a top-to-bottom direction, or along a path that combines both side-to-side and top-to-bottom aspects. In certain embodiments, the cam follower slot may be characterized as extending in a direction transversely to the desired direction of movement of the working tool. The cam follower slot may be aligned with the axis, or may be offset therefrom. A wall may separate the elongated slot from the frame receiving recesses. Alternatively, the recesses and elongated slot could be continuous so long as the recesses are sufficiently narrower than the elongated slot at their junction, forming a reduced dimension which would act to stop movement of the working tool relative to the shaft. In certain embodiments, the elongated slot may be eliminated and the cam follower slot provided at the anterior end face. The instrument is not limited to the drive system described and other cam and cam follower arrangements are contemplated. Further, other rotary-to-linear translation systems may be employed including, without limitation, rack and pinion systems, eccentric cam systems, and shaft and bevel gear systems. Although described in connection with a manual arrangement for driving the rotary-to-linear translation system, a mechanical drive system or a power drive system may, alternatively, be used as would be apparent to one of skill in the art. Further, it also is contemplated that the drive system could be arranged to provide movement of the working tool in a distal-proximal direction.

The frame may be permanently attached to the instrument or, preferably, may be removeable, such that the frame and working tool may constitute a separate unit. The removeable frame and working tool embodiments allow a different size or type of working tool to be employed with the same instrument body, or the same working tool to be removed, perhaps for cleaning or for some other reason, and then reconnected if desired. As shown, a mount 70 may be provided on the outer tube which may include an opening for receiving the proximal segment of the frame legs. The thinner proximal segment is resilient and may be compressed by hand into a slender profile that is insertable into the mount. The intermediate and distal segments (first and second converging segments) may have a more robust configuration, as shown, to ensure adequate support for the working tool. The proximal segment of the legs may include a cam feature 71, such as the wedge shape shown, to facilitate reduction of the legs as the frame is inserted into the mount. The legs may include a latch 72, such as a shoulder located at the end of the cam, as illustrated, which springs back and engages the mount upon clearing the mount end. The legs may also include a second latch, such as an opposed shoulder 74 that locks against the other end of the mount. To release the frame and working tool unit from the instrument, the legs are compressed until the latches 72 are narrower than the mount, and then the reduced frame may be withdrawn. The arrangements for engaging the frame and mount are not limited to the embodiment just described, as should be apparent to one of skill in the art, and other approaches are contemplated including, without limitation, push-button detents, snap-lock structures, and male/female locking systems. The mount may be in the form of a bracket, as illustrated, or may be embodied in other forms that are suitable for supporting the frame. The mount may be integrally formed with the outer tube or may be a separate component that is then associated with the outer tube.

The working tool, preferably formed of metal, is configured for insertion between adjacent vertebrae and includes at least one surface that is arranged with working implements 90 for preparing the vertebral endplate surface. As observed earlier, certain spinal implants may include fixation features for securing the implant either temporarily or permanently and, for example, may provide increased resistance to shear and rotation. The working implements may prepare the endplate surface for receipt and/or engagement with the fixation features or otherwise prepare the endplate surface for insertion of the spinal implant and/or to facilitate osseointegration therewith, or for other purposes as may be desired. The working implements may include one or more projections extending from the surface of the working tool and may be in the form, without limitation, of the following: rasp, cutter, file, grinder, chisel, shaver, reamer, awl, probe or borer. The working implements may be provided on a single surface, on two surfaces, which may include a first surface 92 and a second surface 94, or on more than two surfaces. The instrument is not limited to the number of surfaces bearing working implements. The type and pattern of working implements may be the same on the first and second surfaces or may be arranged differently. Further a combination of different working implements may be provided on a working tool surface. The working implements may be arranged on a top and/or a bottom surface of the working tool and, further or alternatively, may include working implements on a side surface and/or front and back end faces. The surface of the working tool also may include channels for removing debris formed by the working implements. In the embodiment shown, the height of each working surface increases from an outer portion towards the center, providing a dome-like shape. The overall thickness of the working tool may be greater at the proximal end as compared to the distal end, and such thickness may gradually decline from the proximal end towards the distal end. The shapes and dimensions of the working tool are not limited to the embodiments shown or described, and other arrangements are contemplated as should be apparent to one of skill in the art. Each of the surfaces illustrated in FIGS. 1a-1e and 2a-2e includes implements for forming a dome shape and implements for forming recesses for receiving fixation features and/or projections of a spinal disc implant.

Figure 3A:
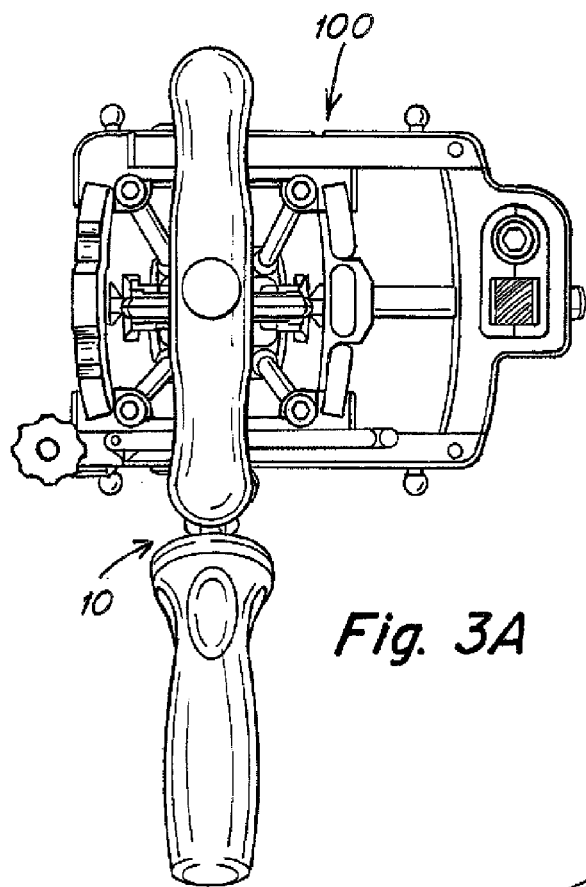
FIGS. 3a-3b are views of a surgical instrument for preparing a vertebral surface mounted through an associated vertebrae distractor.
Figure 3B:
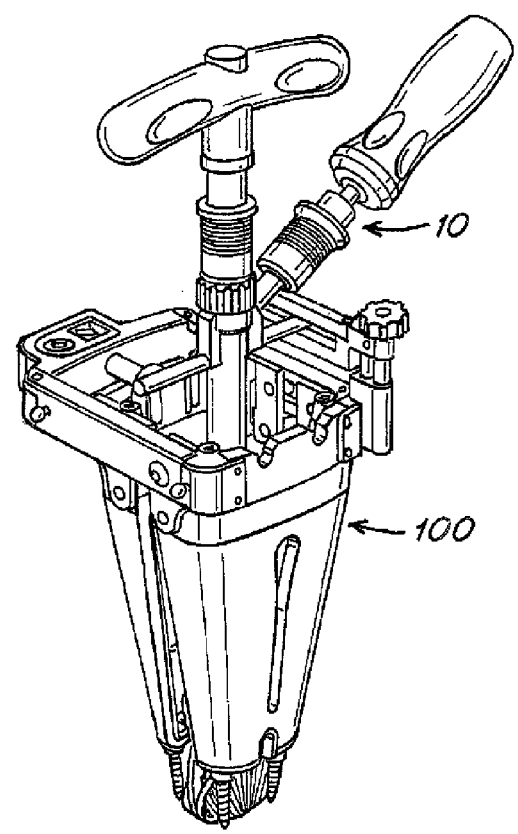

As shown in FIGS. 3a-3b, the endplate preparation instrument may be used with an associated device such as a distractor 100, to prepare a vertebral endplate prior to placement of a spinal disc implant. Adjacent vertebrae are separated by the distractor, providing access to the disc space therebetween. The working end of the instrument is introduced into the distractor with the alignment fins cooperating with the alignment features of the distractor. The depth stop rods may be coordinated with the depth positioning system, allowing the user to control the position of the working end relative to the disc space between the distracted vertebrae. The positioning handle may be removed from the instrument, expanding the field of view. The functional handle is rotated by the physician, causing the working tool to sweep back and forth. As a result, the preparation implements on the surface of the working tool act against and prepare the endplate surface. Recesses and other shapes ultimately form in the endplate surface that are compatible with fixation projections/features of a spinal disc implant. The endplate preparation instrument is removed from the distractor, and the spinal disc implant procedure then may continue.

Figure 4A:
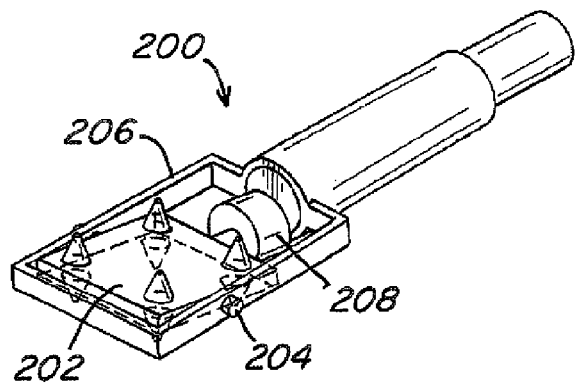
FIGS. 4a-4c are views of a surgical instrument for preparing a vertebral surface, with the instrument arranged to move in a top-to-bottom direction against the vertebral surface.
Figure 4B:
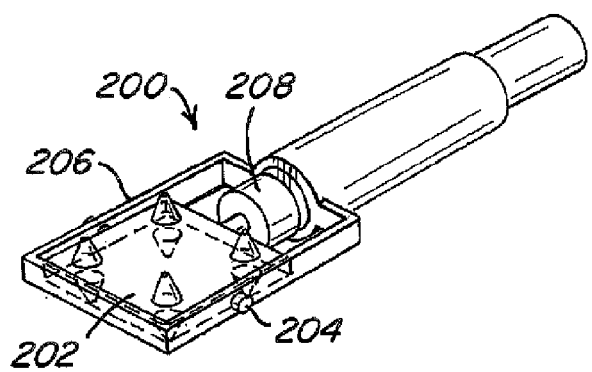
Figure 4C:
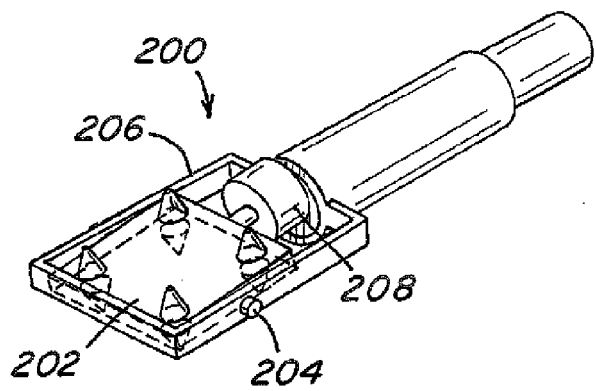

An endplate preparation instrument 200 arranged for movement of a working tool 202 in a top-to-bottom direction is illustrated in FIGS. 4a-4c. Such top-to-bottom directional movement may facilitate penetration of the endplate, or other working action in the direction of the endplate, whether to accommodate a fixation feature or for some other purpose. This working motion may be particularly suitable for preparing a cervical vertebral endplate, for receipt of a cervical spinal disc implant.

The basic components of instrument 200 may be similar to the instrument 100 described in connection with FIGS. 1a-1e and 2a-2e, and may include a working tool, a frame, an outer tube, drive shaft, cam and cam follower, a functional handle, a positioning handle and a mount for the working tool frame on the outer tube, any of the foregoing modified as appropriate for the top-to-bottom directional movement of the working tool. Further, the variations of these and other components and features described in connection with the instrument 100 also may be incorporated in the instrument 200, as appropriate, and as should be apparent to one of skill in the art. Thus, the instrument 200 is not limited to the embodiment illustrated; for example, and without limitation, other rotary-to-linear drive arrangements are contemplated, the sweep axis may be provided along a centerline of the working tool, or offset therefrom, different working tools may be employed to provide different sweep angles, and the working tool and frame may be provided as a unit that is removeable from the instrument.

The working tool shown is pivotable in the top and bottom directions about a sweep axis, and includes working implements for acting against the vertebral endplate surface. The working tool may include a pivot pin 204 that cooperates with a complementary feature in a frame 206. An anterior end 208 of the working tool may include a cam follower slot. The cam follower slot extends from side-to-side; that is, in a direction transverse to the desired direction of movement of the working tool. Other arrangements of the cam follower slot are contemplated. A cam pin at the end of the drive shaft mates with the cam follower slot and rotation of the drive shaft moves the working tool in an upward/downward direction against the endplate surface. Although not illustrated, nor necessary for instrument 200, an elongated slot may be provided in a counter-bore relationship to the cam follower slot, elongated in the desired direction of movement of the working tool; so in a top-to-bottom direction and normal to the direction of the cam follower slot. The elongated slot is adapted to receive the distal end of the shaft.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A surgical instrument for preparing an endplate surface of a vertebra, the instrument comprising:
 a working end including a pivot pin and a working tool, said working tool configured for insertion between adjacent vertebras, said working tool having working implements for preparing the vertebral endplate surface, wherein said working tool is arranged at said working end and is associated with said pivot pin for pivoting about said pivot pin, and wherein said working tool includes a cam follower; and
 a rotatable drive shaft having a proximal end and a distal end, said driveshaft including a cam located at said drive shaft distal end, wherein said cam is operatively associated with said cam follower to pivot said working tool about said pivot pin to prepare the vertebral surface in response to rotation of said rotatable drive shaft relative to said working tool and about a longitudinal axis of said rotatable drive shaft, when the rotatable drive shaft is coupled with the working tool, wherein said cam is a cam pin extending from said distal end of said drive shaft, wherein said cam follower is a cam follower slot provided in said working tool, wherein said cam follower slot is adapted to receive said cam pin, wherein said working tool includes an elongated slot that is counter-bored with respect to said cam follower slot, wherein said elongated slot is adapted to receive said distal end of said drive shaft, wherein said elongated slot and said cam follower slot extend in different directions, and wherein said working tool pivots about said pivot pin relative to said rotatable drive shaft.

2. The surgical instrument recited in 1, wherein said working tool includes an anterior end and said counter-bored elongated slot is located at said interior end.

3. The surgical instrument recited in 1, wherein said working end further includes a frame configured to mount to said working tool.

4. The surgical instrument recited in 3, wherein said pivot pin extends between said working tool and said frame.

5. The surgical instrument recited in 4, wherein said frame and said working tool are removable as a unit from said instrument.

6. The surgical instrument recited in 5, wherein said working tool includes a recess for receiving a portion of said frame, at least one interior surface of said working tool being exposed by said recess, and said pivot pin is located on said at least one interior surface.

7. The surgical instrument recited in 6, wherein said at least one interior surface comprises a pair of opposed interior surfaces of said working tool exposed by said recess, and said pivot pin extends between said pair of opposed interior surfaces.

8. The surgical instrument recited in 3, wherein said working tool has a farthest extent of sweep in a first direction and in a second direction, and said working tool projects beyond said frame when said working tool is in its farthest extent of sweep in said respective directions.

9. The surgical instrument recited in 1, further including a tube, wherein said drive shaft extends within said tube.

10. The surgical instrument recited in 9, further including a frame configured to mount to said working tool, and a mount associated with said tube configured to support said frame.

11. The surgical instrument recited in 10, wherein said frame is removably engaged to said tube associated mount.

12. The surgical instrument recited in 11, further including a handle coupled to said drive shaft.

13. The surgical instrument recited in claim 1, wherein said cam is operatively associated with said cam follower to pivot said working tool from top-to-bottom.

14. The surgical instrument recited in claim 1, wherein said cam is operatively associated with said cam follower to pivot said working tool about a path that includes side-to-side and top-to-bottom aspects.

15. A surgical instrument for preparing an endplate surface of a vertebra, the instrument comprising:
 an elongated tube;
 a rotatable drive shaft having a proximal end and a distal end, said drive shaft including a cam located at said drive shaft distal end;
 a working tool configured for insertion between adjacent vertebras and having at least one surface with a working implement for preparing the vertebral endplate surface, said working tool being arranged for pivotal movement in at least one of a side-to-side direction and a top-to-bottom direction relative to said rotatable drive shaft, and wherein said working tool includes a cam follower;
 a frame connected to said tube and mounting said working tool; and
 a mount supported by said tube for engaging with said frame, said cam and said cam follower being coupled when said mount and said frame are engaged, whereby rotation of said rotatable drive shaft about a longitudinal axis of said rotatable drive shaft, when said cam and cam follower are coupled with each other, causes said working tool to pivot in at least one of said side-to-side direction and said top-to-bottom direction, wherein said working tool includes an elongated slot that is counter-bored with respect to said cam follower, wherein the elongated slot is adapted to receive said distal end of said drive shaft, wherein said cam is a cam pin extending from said distal end of said drive shaft, wherein said cam follower is a cam follower slot provided in said working tool, wherein said cam follower slot is adapted to receive said cam pin, and wherein said elongated slot and said cam follower slot extend in different directions.

16. The surgical instrument recited in 15, wherein said frame and said working tool are removable as a unit from said instrument.

17. The surgical instrument recited in 15, wherein said working tool includes a recess for receiving a portion of said frame, at least one interior surface of said working tool being exposed by said recess, and a pivot pin located on said at least one interior surface.

18. The surgical instrument recited in 17, wherein said at least one interior surface comprises opposed interior surfaces of said working tool exposed by said recess, and a pivot pin extends between said opposed interior surfaces.

19. The surgical instrument recited in 15, wherein said working tool has a farthest extent of sweep in a first direction and in a second direction, and said working tool projects beyond said frame when said working tool is in its farthest extent of sweep in said respective directions.

20. The surgical instrument recited in 15, further including a handle coupled to said drive shaft.

21. The surgical instrument recited in claim 15, wherein said frame has a planar form and a U-shape.

22. The surgical instrument recited in claim 21, wherein said frame includes a pair of legs, each leg having a proximal segment including a latch for engaging with said mount.

23. The surgical instrument recited in claim 22, wherein each of said pair of legs further includes a second latch in opposition to said proximal segment latch.

24. The surgical instrument recited in claim 15, wherein said frame includes a pair of legs, each of said pair of legs including a proximal segment, a first converging segment and a second acutely converging segment, and said pair of legs coincide at a junction of said second acutely converging segments along which is located a sweep axis of said working tool.

25. The surgical instrument recited in claim 22, wherein the proximal segment of each leg includes a cam feature to facilitate inward compression of said proximal segment during entry into the mount on the surgical instrument body.

26. The surgical instrument recited in claim 22, wherein each of said pair of legs further includes a first converging segment and a second acutely converging segment, with said pair of legs coinciding at a junction of said second acutely converging segments along which is located a sweep axis of said working tool.

27. The surgical instrument recited in claim 26, wherein said frame includes an inwardly extending shoulder proximal of said first converging segment.

28. The surgical instrument recited in claim 22, wherein each of said pair of legs includes an outwardly bowed proximal segment.

29. The surgical instrument recited in claim 15, wherein said frame has a distal end that defines a compound opening including a distal triangular shape and a proximal quadrilateral shape.

30. The surgical instrument recited in claim 15, wherein said working tool includes a recess defining a standoff, said standoff having a compound shape including a distal triangular shape and a proximal quadrilateral shape.

31. The surgical instrument recited in claim 15, wherein said frame includes a centerline and a sweep axis of said working tool is normal to and aligned with said centerline.

32. The surgical instrument recited in claim 15, wherein said working tool is arranged for movement about a path that includes side-to-side and top-to-bottom aspects.

33. The surgical instrument recited in claim 1, wherein said cam is operatively associated with said cam follower to pivot said working tool from side-to-side.

34. A surgical instrument for preparing an endplate surface of a vertebra, the instrument comprising:
a working end including a working tool configured for insertion between adjacent vertebras, said working tool having working implements for preparing the vertebral endplate surface and being arranged at said working end for movement in a combination of a side-to-side direction and a top to-bottom directions, wherein the working tool includes a counter-bored elongated slot and a cam follower slot located in the counter-bored elongated slot, and wherein the elongated slot and the cam follower slot extend in different directions;
a rotatable drive shaft having a proximal end and a distal end, a cam pin extending from the distal end of the drive shaft, wherein the distal end of the driveshaft is received in the counter-bored elongated slot and the cam pin is received in the cam follower slot, wherein the working tool moves in the combination of the side-to-side direction and the top-to-bottom direction to prepare the vertebral endplate surface in response to rotation of the rotatable drive shaft relative to the cam follower slot and about a longitudinal axis of said rotatable drive shaft, when the rotatable drive shaft is coupled with the working tool, and wherein the working tool is arranged for movement in the combination of side-to-side direction and top-to-bottom direction relative to the rotatable drive shaft.

* * * * *

UNITED STATES PATENT AND TRADEMARK OFFICE
CERTIFICATE OF CORRECTION

PATENT NO.        : 8,876,828 B2
APPLICATION NO.   : 12/428801
DATED             : November 4, 2014
INVENTOR(S)       : Jonathan Lawson et al.

Page 1 of 1

It is certified that error appears in the above-identified patent and that said Letters Patent is hereby corrected as shown below:

In The Claims
At column 8, claim 2, line 3, "said interior end" should read --said anterior end--.

Signed and Sealed this
Tenth Day of February, 2015

Michelle K. Lee
*Deputy Director of the United States Patent and Trademark Office*